United States Patent
Yahagi et al.

(10) Patent No.: US 9,033,978 B2
(45) Date of Patent: May 19, 2015

(54) HIGH-FREQUENCY TREATMENT INSTRUMENT

(75) Inventors: Naohisa Yahagi, Tokyo (JP); Yuta Muyari, Tokyo (JP); Tsutomu Nakamura, Tokyo (JP); Chika Miyajima, Tokyo (JP); Tsutomu Okada, Tokyo (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 1753 days.

(21) Appl. No.: 11/810,372

(22) Filed: Jun. 5, 2007

(65) Prior Publication Data

US 2007/0282328 A1    Dec. 6, 2007

(30) Foreign Application Priority Data

Jun. 5, 2006 (JP) ................ P2006-156392

(51) Int. Cl.
*A61B 18/14* (2006.01)
*A61B 17/3205* (2006.01)
*A61B 17/221* (2006.01)
(Continued)

(52) U.S. Cl.
CPC ....... *A61B 18/1402* (2013.01); *A61B 17/32056* (2013.01); *A61B 2017/2212* (2013.01); *A61B 2018/141* (2013.01); *A61B 18/1492* (2013.01); *A61B 2017/00269* (2013.01); *A61B 2018/00214* (2013.01); *A61B 2018/00898* (2013.01); *A61B 2018/1407* (2013.01); *A61B 2018/144* (2013.01); *A61B 2018/1475* (2013.01)

(58) Field of Classification Search
CPC ............... A61B 2018/1405; A61B 2018/1407; A61B 2018/141; A61B 2018/144; A61B 2018/1475; A61B 2017/00358; A61B 2017/2212; A61B 2017/2217; A61B 17/32056; A61B 17/221; A61B 2017/00269; A61B 2018/20
USPC .................................. 606/45–47, 49, 113
See application file for complete search history.

(56) References Cited

U.S. PATENT DOCUMENTS 3,805,791 A * 4/1974 Seuberth et al. ................ 606/47
3,955,578 A * 5/1976 Chamness et al. ............. 606/47
(Continued)

FOREIGN PATENT DOCUMENTS

JP    S53-105888    9/1978
JP    S62-064355    3/1987
(Continued)

OTHER PUBLICATIONS

Japanese Official Action dated Mar. 9, 2010 together with an English language translation.
(Continued)

*Primary Examiner* — Jaymi Della
(74) *Attorney, Agent, or Firm* — Scully, Scott, Murphy & Presser, P.C.

(57) ABSTRACT

A high-frequency treatment instrument having a sheath; an elongated extension member; a narrow portion provided on an inner surface of the sheath; and a pressing member which allows the elongated extension member to advance and retract only in a part of the sheath. The elongated extension member is advanced to form a first treatment electrode extending along a central axial line of the sheath and the elongated extension member is further advanced to form a second treatment electrode which intersects with the central axial line of the sheath.

2 Claims, 18 Drawing Sheets

(51) Int. Cl.
*A61B 17/00* (2006.01)
*A61B 18/00* (2006.01)

(56) References Cited

U.S. PATENT DOCUMENTS

| | | | |
|---|---|---|---|
| 4,181,131 A | | 1/1980 | Ogiu |
| 4,202,338 A | * | 5/1980 | Bitrolf ............................ 606/47 |
| 4,643,187 A | * | 2/1987 | Okada ............................. 606/47 |
| 4,718,419 A | | 1/1988 | Okada |
| 5,437,665 A | | 8/1995 | Munro |
| 6,015,415 A | * | 1/2000 | Avellanet ...................... 606/113 |
| 6,221,039 B1 | * | 4/2001 | Durgin et al. .................. 604/22 |
| 6,395,001 B1 | | 5/2002 | Ellman et al. |
| 6,402,740 B1 | * | 6/2002 | Ellis et al. ....................... 606/28 |
| 6,929,642 B2 | | 8/2005 | Xiao et al. |
| 7,758,593 B2 | * | 7/2010 | Nobis et al. .................. 606/113 |
| 2004/0002702 A1 | | 1/2004 | Xiao et al. |
| 2004/0172018 A1 | | 9/2004 | Okada |
| 2006/0064113 A1 | | 3/2006 | Nakao |

FOREIGN PATENT DOCUMENTS

| | | |
|---|---|---|
| JP | H05-211994 | 8/1993 |
| JP | H08-299355 | 11/1996 |
| JP | 2000-185053 | 7/2000 |
| JP | 2000-508561 | 7/2000 |
| JP | 2004-261372 | 9/2004 |
| JP | 2005-348844 | 12/2005 |
| WO | WO 97/38637 | 10/1997 |
| WO | WO 99/42041 | 8/1999 |

OTHER PUBLICATIONS

Japanese Office Action dated Nov. 16, 2010.
Chinese Office Action dated Nov. 16, 2010.
Official Action mailed Feb. 15, 2011 from the Japan Patent Office in counterpart Japanese Patent Application No. 2006-156392, together with a partial English language translation.

* cited by examiner

A-A CROSS SECTION

B-B CROSS SECTION

HIGH-FREQUENCY TREATMENT INSTRUMENT

BACKGROUND OF THE INVENTION

1. Field of the Invention

The present invention relates to a high-frequency treatment instrument.

Priority is claimed on Japanese Patent Application No. 2006-156392, filed on Jun. 5, 2006, the content of which is incorporated herein by reference.

2. Description of the Related Art

As a treatment method of removing a biological tissue such as a mucous membrane by the use of an endoscope, in order to remove the pathological lesion portion generated on a surface of an alimentary canal, an endoscopic submucosal dissection (ESD) method of cutting out a normal mucous membrane around a pathological lesion portion and then dissecting a submucosal layer and remove the pathological lesion portion, for example, is known.

Various treatment instruments are used for such kind of dissecting treatment. For example, a high-frequency treatment instrument having a knife portion as a treatment electrode at a distal end of a rod-shaped electrode portion housed in a sheath is known (for example, see Japanese Unexamined Patent Application, First Publication No. H08-299355).

By the use of the high-frequency treatment instrument described in Japanese Unexamined Patent Application, First Publication No. H08-299355, it is possible to dissect the submucosal layer by allowing high-frequency current to flow in the knife portion to cut out a mucous membrane contacting the knife portion.

SUMMARY OF THE INVENTION

In a first aspect of the high-frequency treatment instrument of the present invention, there is provided a high-frequency treatment instrument for performing a high-frequency treatment on a target tissue, the high-frequency treatment instrument includes: a sheath; a pair of arm portions which is disposed in the sheath so as to freely extend and retract, is in a closed state in the sheath, and is opened in a direction away from a center axial line of the sheath when it protrudes from a distal end of the sheath; and a linear treatment electrode which is connected to distal end sides of the pair of arm portions and which is stretched between the arm portions when the pair of arm portions is opened.

In a second aspect of the high-frequency treatment instrument of the present invention, at least a part of the treatment electrode may be stretched in a bent state when the pair of arm portions is opened.

In a third aspect of the high-frequency treatment instrument of the present invention, at least one of the pair of arm portions is formed in a tube shape, and the treatment electrode is relatively fixed to the other of the pair of arm portions and is disposed to extend and retract in the one of the pair of arm portions.

In a fourth aspect of the high-frequency treatment instrument of the present invention, the high-frequency treatment instrument further includes an elongated extension member disposed to extend in the sheath so as to freely extend and retract in which the sheath communicates with the one of the pair of arm portions and one end of the treatment electrode is connected to the elongated extension member.

In a fifth aspect of the high-frequency treatment instrument of the present invention, there is provided a high-frequency treatment instrument including: an elongated extension member having an axial core; a pair of arm portions which is disposed at a distal end of the elongated extension member and which can be opened and closed relative to the axial core; and a linear treatment electrode which is connected to distal ends of the pair of arm portions, which is folded when the pair of arm portions is closed, and which is stretched between the arm portions when the pair of arm portions is opened.

In a sixth aspect of the high-frequency treatment instrument of the present invention, there is provided a high-frequency treatment instrument which further includes a sheath through which the pair of arm portions is inserted to freely extend and retract and the distal end sides of the pair of arm portions is urged to move away from the axial core such that a distance therebetween becomes larger than the outer diameter of the sheath.

In a seventh aspect of the high-frequency treatment instrument of the present invention, there is provided a high-frequency treatment instrument including: a sheath; and an elongated extension member which is disposed in the sheath so as to freely extend and retract and which has a first linear portion disposed along the sheath, a first bent portion formed at a distal end of the first linear portion, a second linear portion extending from the first bent portion, and a second bent portion formed halfway along the second linear portion.

In an eighth aspect of the high-frequency treatment instrument of the present invention, there is provided a high-frequency treatment instrument, when the first linear portion and the second linear portion are made to extend toward the distal end direction of the sheath and thus the first bent portion and the second bent portion are made to protrude from the sheath, a treatment electrode intersecting with a center axial line of the sheath is formed between the first bent portion and the second bent portion.

In a ninth aspect of the high-frequency treatment instrument of the present invention, there is provided a high-frequency treatment instrument in which a control portion for controlling a protruding amount of the first linear portion and the second linear portion from the distal end of the sheath is disposed in the first linear portion and the second linear portion which are closer to a proximal end side than the second bent portion.

DETAILED DESCRIPTION OF THE INVENTION

Figure 1:
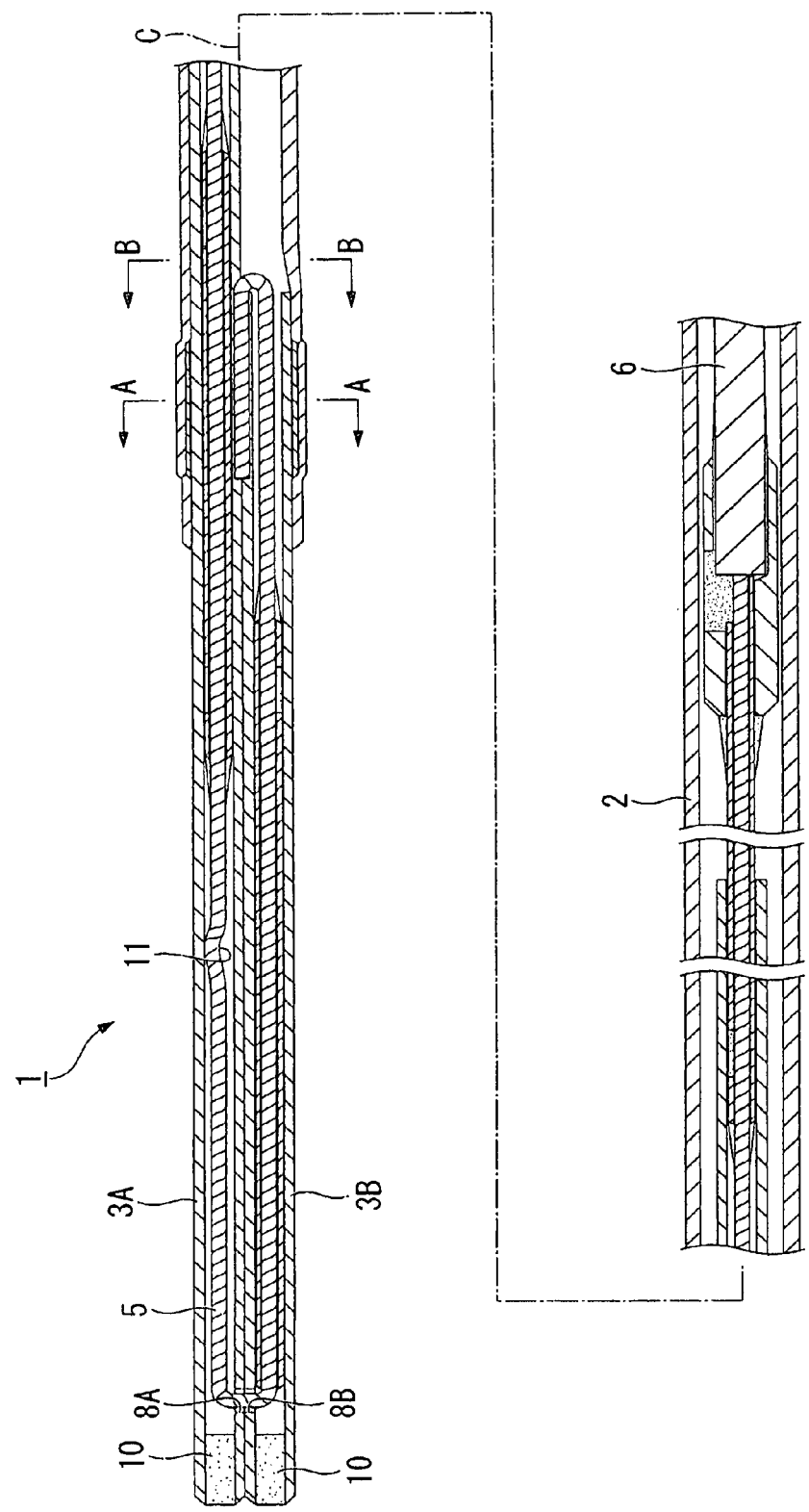
FIG. 1 is a sectional view of substantial part illustrating a high-frequency treatment instrument according to a first embodiment of the invention.
Figure 2A:
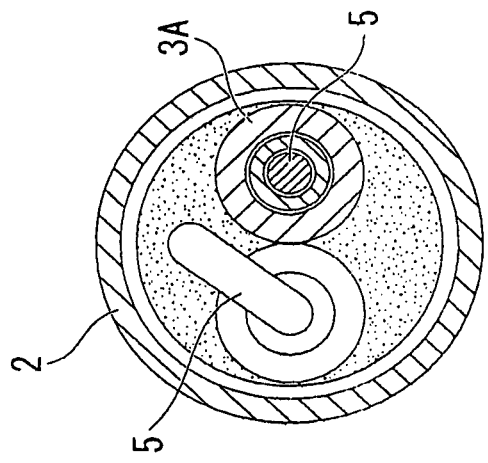
FIG. 2A is a cross-sectional view taken along line A-A of FIG. 1.
Figure 2B:
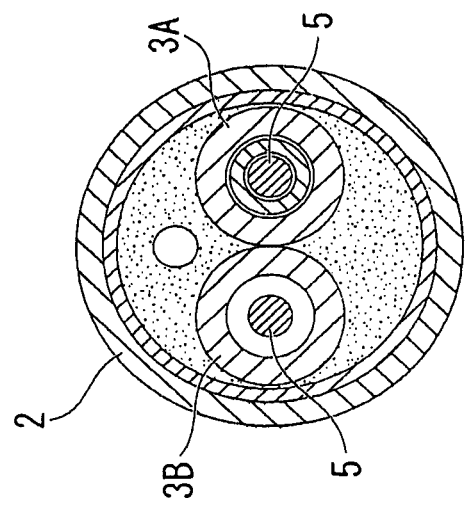
FIG. 2B is a cross-sectional view taken along line B-B of FIG. 1.
Figure 3:
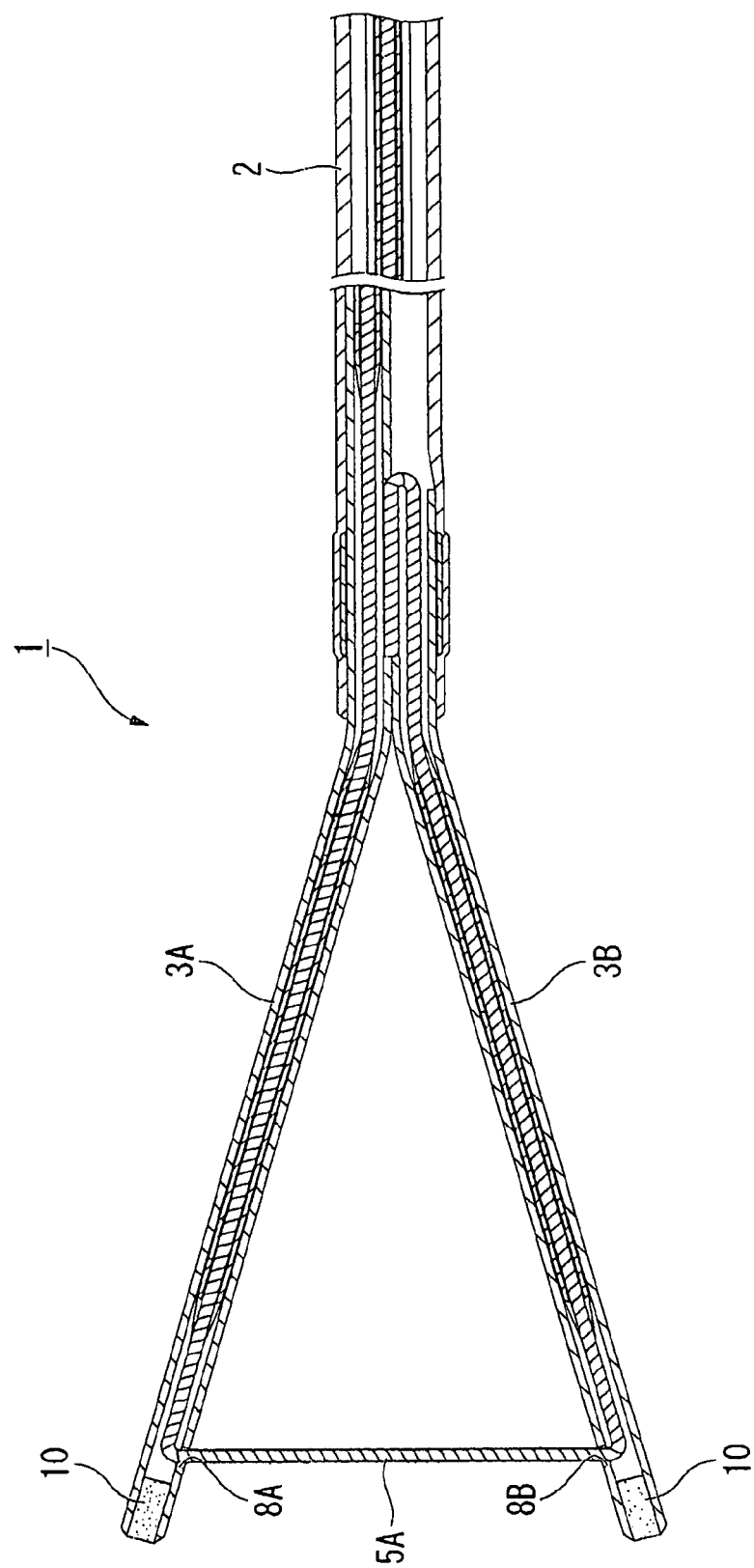
FIG. 3 is a sectional view of substantial part illustrating the high-frequency treatment instrument according to the first embodiment of the invention.
Figure 4:
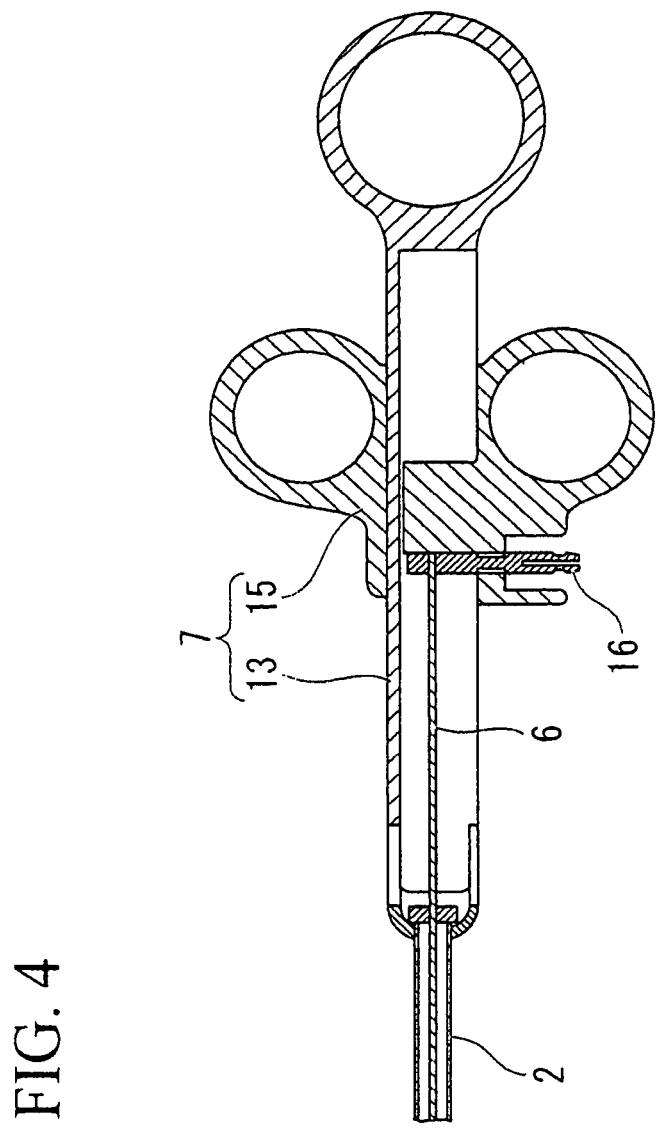
FIG. 4 is a sectional view illustrating an operating portion of the high-frequency treatment instrument according to the first embodiment of the invention.

A first embodiment of the invention will be described with reference to FIGS. 1 to 8.

A high-frequency treatment instrument 1 according to the first embodiment of the invention is a high-frequency treatment instrument for performing a high-frequency treatment on a pathological lesion portion (target tissue) not shown and includes an elongated flexible sheath 2, a pair of arm portions 3A and 3B which is disposed in the sheath 2 so as to freely extend and retract, which is in a closed state in the sheath 2, and which is stretched in a direction moving away from a center axial line C of the sheath 2 when it protrudes from the distal end of the sheath 2, a linear treatment electrode 5 which is connected to the distal end sides of the pair of arm portions 3A and 3B and which is stretched between the arm portions 3A and 3B when the pair of arm portions 3A and 3B are opened, an operating wire (elongated extension member) 6 which is disposed to be extended in the sheath 2 so as to freely extend and retract and the distal end of which is connected to the treatment electrode 5, and an operating portion 7 to which the proximal ends of the sheath 2 and the operating wire 6 are connected and which operates the operating wire 6 to extend and retract relative to the sheath 2, as shown in FIGS. 1 to 4.

The sheath 2 has such an outer diameter that it can be inserted through a treatment instrument channel of an endoscope not shown.

The pair of arm portions 3A and 3B is both formed in a tube shape and is communicated with the sheath 2. At least in the vicinity of the distal end of the sheath 2, the pair of arm portions 3A and 3B is flexibly provided to be curved relative to the sheath 2. Insertion holes 8A and 8B through which the treatment electrode 5 can be inserted are formed in the distal end sides of the pair of arm portions 3A and 3B in the locations opposing each other when the pair of arm portions 3A and 3B are closed. The distal ends of the pair of arm portions 3A and 3B are sealed with sealing members 10.

The proximal end side of one of the pair of arm portions 3A extends to the vicinity of the distal end of the operating wire 6.

The treatment electrode 5 is formed in a wire shape, is inserted through one of the pair of arm portions 3A so as to extend and retract, protrudes from the insertion hole 8A, and is inserted through the other of the pair of arm portions 3B from the insertion hole 8B of the other of the pair of arm portions 3B. The distal end of the treatment electrode 5 is fixed in a folded-back state to a position where the pair of arm portions 3A and 3B is connected to the sheath 2. Accordingly, the treatment electrode 5 is disposed to freely extend and retract in one of the pair of arm portions 3A and is relatively fixed in the other of the pair of arm portions 3B.

In the treatment electrode 5 located in the insertion hole 8A of one of the pair of arm portions 3A when the pair of arm portions 3A and 3B are opened at a predetermined opening angle, a bent portion 11 which engages the insertion hole 8A so as to control the extend and retract movement of the treatment electrode 5 is formed.

The operating portion 7 includes an operating portion body 13 connected to the proximal end of the sheath 2 and a slider 15 to which the proximal end of the operating wire 6 is connected and which can freely slide relative to the operating portion body 13. In the slider 15, an electrode terminal 16 which is electrically connected to the operating wire 6 and which is connected to a connection cable extending from a high-frequency power source not shown is disposed.

Next, operations of the high-frequency treatment instrument 1 will be described with reference to a procedure of removing a pathological lesion portion X generated on the surface of an alimentary canal by dissecting a submucosal layer W by the high-frequency treatment instrument 1 according to this embodiment.

Figure 5:
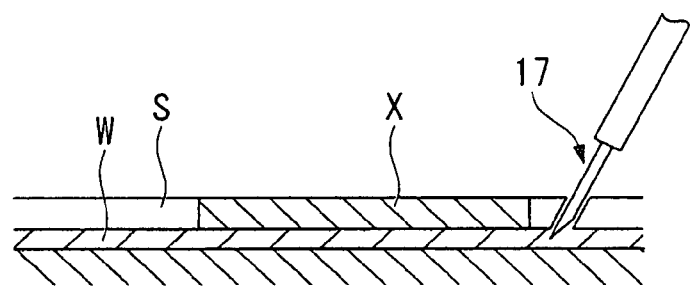
FIG. 5 is an explanatory diagram illustrating a usage example of the high-frequency treatment instrument according to the first embodiment of the invention.
Figure 6:
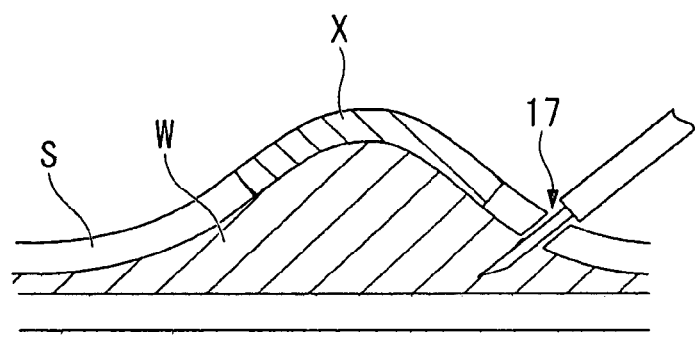
FIG. 6 is an explanatory diagram illustrating a usage example of the high-frequency treatment instrument according to the first embodiment of the invention.

First, as shown in FIG. 5, an injection needle 17 is introduced into a body cavity through a treatment instrument channel of an endoscope not shown and a physiologic saline solution is locally injected into the submucosal layer W in the vicinity of the pathological lesion portion X to be removed, thereby distending the pathological lesion portion X as shown in FIG. 6. Before performing the local injection, it is preferable that a dye be applied around the pathological lesion portion X to clarify the boundary of the pathological lesion portion X, and then a mucous membrane S is marked at a plurality of positions surrounding the circumference of the pathological lesion portion X by the use of an existing high-frequency knife 18.

Figure 7:
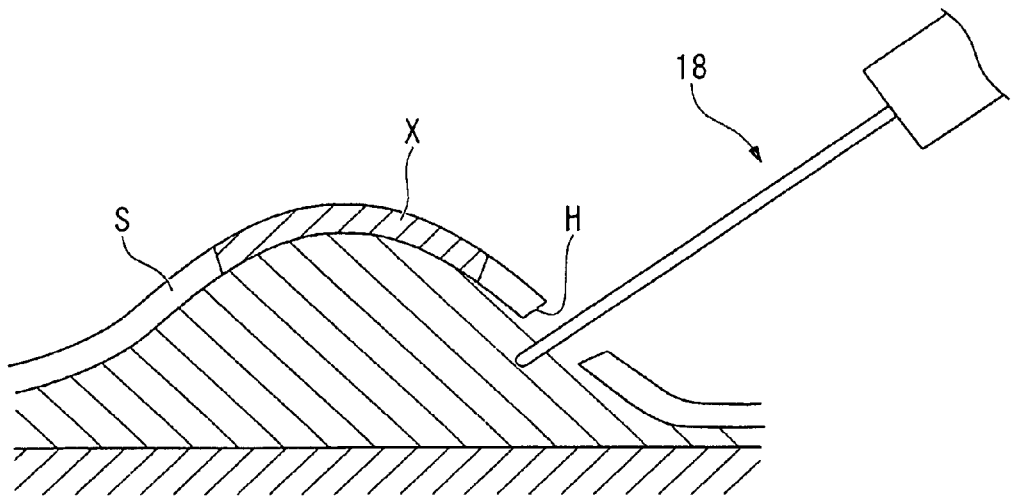
FIG. 7 is an explanatory diagram illustrating a usage example of the high-frequency treatment instrument according to the first embodiment of the invention.

Next, the existing high-frequency knife 18 is inserted through the treatment instrument channel and is brought into contact with a part of the mucous membrane S in the vicinity of the pathological lesion portion X as shown in FIG. 7, and a hole H which is a starting point of the entire peripheral cut-out is formed by supplying high-frequency current thereto. By operating both the endoscope and the high-frequency knife, the mucous membrane around the pathological lesion portion X is cut out to expose the submucosal layer W.

Subsequently, the high-frequency knife is pulled out of the channel and the high-frequency treatment instrument 1 is inserted into the channel. Then, with the pair of arm portions 3A and 3B protruding from the distal end of the channel, the slider 15 of the high-frequency treatment instrument 1 is made to extend relative to the operating portion body 13. At this time, the operating wire 6 extends toward the distal end direction of the sheath 2 relative to the sheath 2.

Here, since the distal end of the treatment electrode 5 is fixed to the vicinity of the distal end of the sheath 2, the treatment electrode 5 is pushed in a compressing direction and one of the pair of arm portions 3A and the other of the pair of arm portions 3B are separated from each other as a reaction thereto, thereby opening the pair of arm portions 3A and 3B. Then, the bent portion 11 formed in the treatment electrode 5 engages the insertion hole 8A of the one of the pair of arm portions 3A, whereby the pair of arm portions 3A and 3B are opened at a predetermined opening angle. At this time, a straight line portion 5A substantially perpendicular to the center axial line C of the sheath 2, that is, the extend and retract direction of the operating wire 6 is formed in the treatment electrode 5. Depending on the size of the pathological lesion portion X, the operating wire 6 may be operated to extend and retract to adjust the opening angle of the pair of arm portions 3A and 3B.

Figure 8:
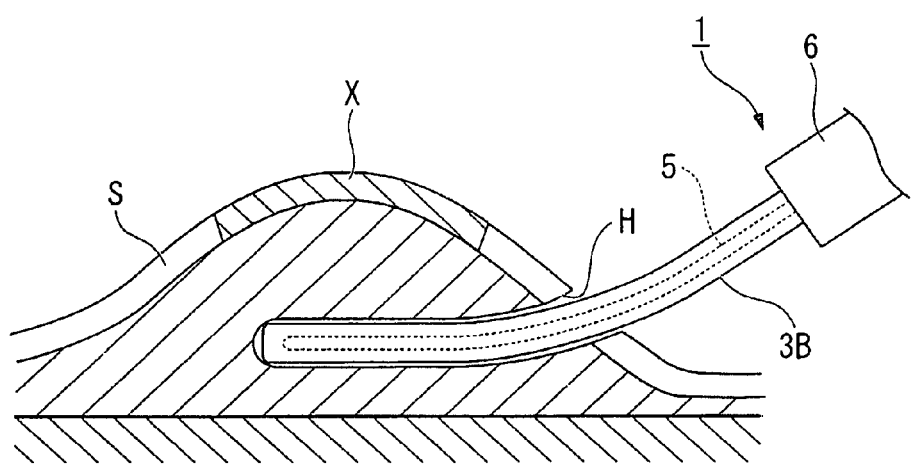
FIG. 8 is an explanatory diagram illustrating a usage example of the high-frequency treatment instrument according to the first embodiment of the invention.

High-frequency current is made to flow while the straight line portion 5A is brought into contact with the submucosal layer W, and the sheath 2 of the high-frequency treatment instrument 1 is made to extend relative to the channel while observing with the endoscope which is in fixed state. In this way, as shown in FIG. 8, the submucosal layer W is cut out to remove the pathological lesion portion X by the straight line portion 5A.

According to the high-frequency treatment instrument 1, when the pair of arm portions 3A and 3B is made to protrude from the distal end of the sheath 2 and is thus opened, the treatment electrode 5 can be stretched in a direction intersecting with the center axial line C of the sheath 2 at the distal end sides of the pair of arm portions 3A and 3B. Accordingly, when the pair of arm portions 3A and 3B is operated to extend and retract relative to the sheath 2 with the treatment electrode 5 stretched, it is possible to increase the contact area between the treatment electrode 5 and the target tissue such as the pathological lesion portion X or the like compared to the conventional technique. Accordingly, it is possible to perform treatments on the target tissue by directly operating the treatment electrode 5, thereby facilitating the procedure.

The pair of arm portions 3A and 3B can be opened and closed by allowing the treatment electrode 5 to extend and retract relative to the sheath 2 via the operating wire 6. When the pair of arm portions 3A and 3B is closed, the treatment electrode 5 can be housed in the pair of arm portions 3A and 3B.

Figure 9:
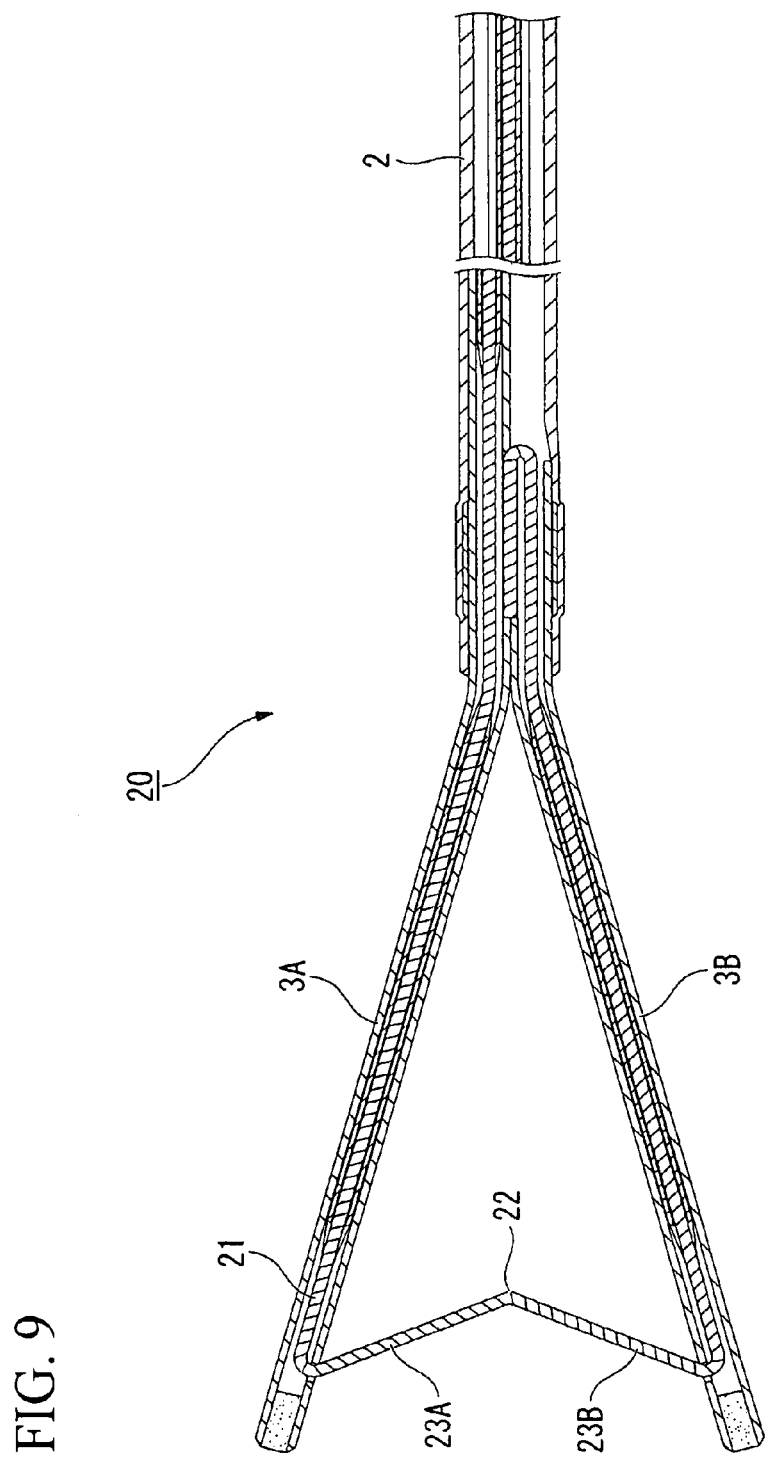
FIG. 9 is a sectional view illustrating a high-frequency treatment instrument according to a second embodiment of the invention.

Next, a second embodiment of the invention will be described with reference to FIG. 9.

The same elements as the first embodiment are denoted by the same reference numerals and descriptions thereof will be omitted.

The second embodiment is different from the first embodiment, in that a part of a treatment electrode 21 of a high-frequency treatment instrument 20 according to the second embodiment is stretched in a bent state when a pair of arm portions 3A and 3B is opened.

In the treatment electrode 21, a bent portion 22 is disposed in a portion corresponding to the straight line portion 5A of the treatment electrode 5 according to the first embodiment. The bent portion 22 is formed to face the distal end of the sheath 2 in a state that the treatment electrode 21 is stretched. That is, since a first straight line portion 23A and a second straight line portion 23B are formed with the bent portion 22 interposed therebetween, the treatment electrode 21 is stretched in a substantially M shape including the portions disposed in the pair of arm portions 3A and 3B.

According to the high-frequency treatment instrument 20, since a target tissue not shown can be interposed in the bent portion 22, it is possible to bring the treatment electrode 21 into stable contact with the target tissue.

Figure 10:
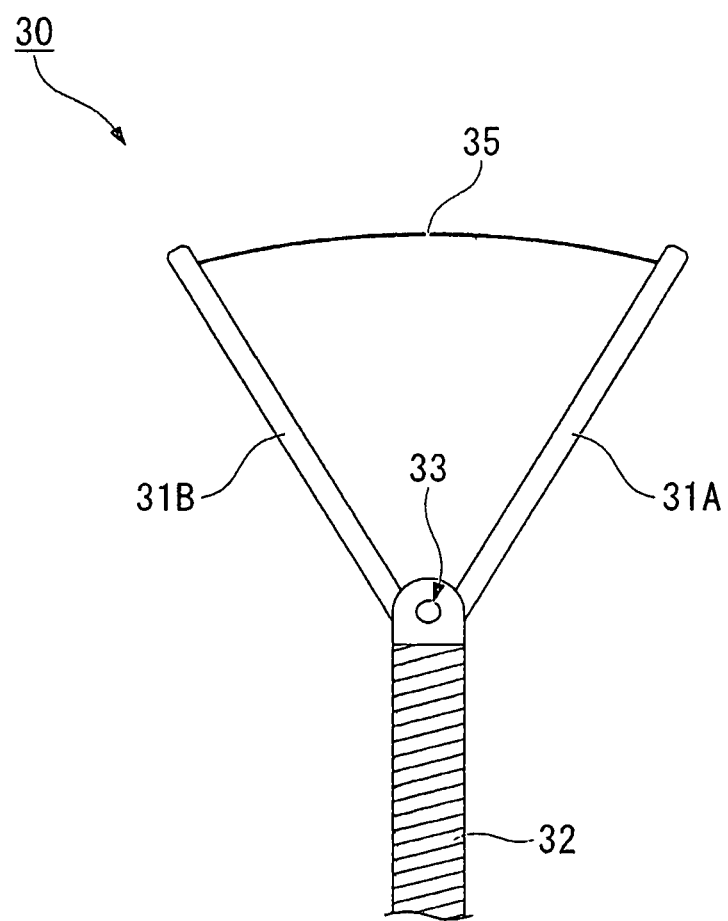
FIG. 10 is a plan view illustrating a high-frequency treatment instrument according to a third embodiment of the invention.

Next, a third embodiment of the invention will be described with reference to FIGS. 10 and 11.

The same elements as the first embodiment are denoted by the same reference numerals and descriptions thereof will be omitted.

The third embodiment is different from the first embodiment, in that a pair of arm portions 31A and 31B of a high-frequency treatment instrument 30 according to the third embodiment freely extends and retracts in a coil sheath (sheath) 32 and is disposed at a distal end of an operating wire (not shown) having an axial core via a link mechanism (not shown) having an axis 33 so as to be opened and closed relative to the axial core, and a treatment electrode 35 is connected to both distal ends of the pair of arm portions 31A and 31B, is folded when the pair of arm portions 31A and 31B is closed, and is stretched between the arm portions 31A and 31B when the pair of arm portions 31A and 31B is opened.

Operations of the high-frequency treatment instrument 30 will be described.

Figure 11A:
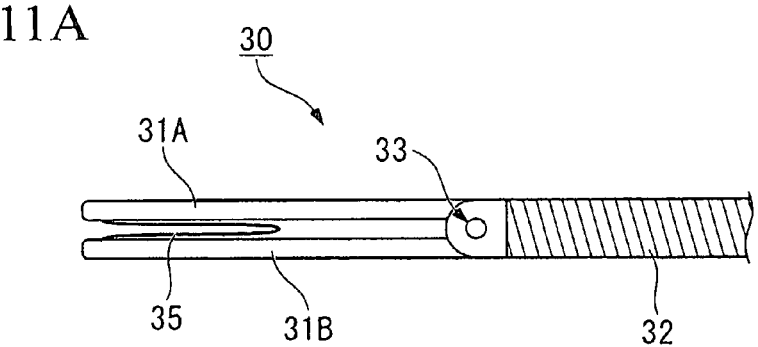
FIG. 11A is a partially-sectional plan view illustrating a closed state of the high-frequency treatment instrument according to the third embodiment of the invention.

As shown in FIG. 11A, when the pair of arm portions 31A and 31B is made to protrude from a treatment instrument channel not shown in a state that the pair of arm portions 31A and 31B is closed and the treatment electrode 35 is folded between the pair of arms 31A and 31B, and is then opened, an operating wire not shown is made to extend toward the distal end side relative to the coil sheath 32.

Figure 11B:
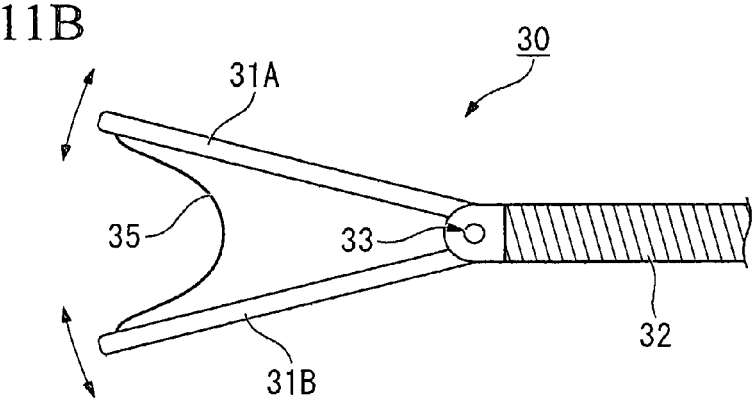
FIG. 11B is a partially-sectional plan view illustrating a state in the way of opening or closing of the high-frequency treatment instrument according to the third embodiment of the invention.
Figure 11C:
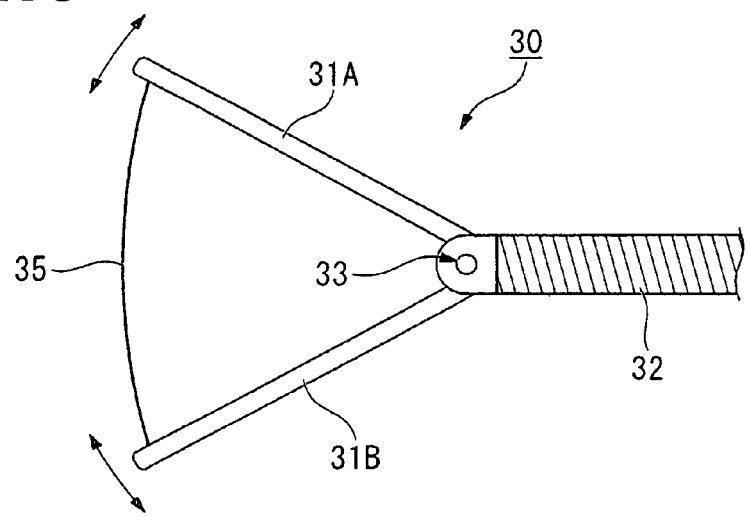
FIG. 11C is a partially-sectional plan view illustrating an opened state of the high-frequency treatment instrument according to the third embodiment of the invention.

At this time, the pair of arm portions 31A and 31B moves away from the axial core of the operating wire 32 via the link mechanism not shown and thus is opened. In this case, as shown in FIG. 11B, both ends of the treatment electrode 35 moves away from each other along with the pair of arm portions 31A and 31B and thus the treatment electrode 35 is gradually stretched. Then, when the pair of arm portions 31A and 31B is opened at a predetermined opening angle, as shown in FIG. 11C, the treatment electrode 35 is stretched between the pair of arm portions 31A and 31B.

When a cut-out operation is finished and the operating wire is made to retract toward the proximal end side of the coil sheath 32 to close the pair of arm portions 31A and 31B, as shown in FIG. 11A, the treatment electrode 35 is housed in a state where it is interposed again between the pair of arm portions 31A and 31B.

According to the high-frequency treatment instrument 30, the same advantages as the first embodiment can be obtained.

Next, a fourth embodiment of the invention will be described with reference to FIGS. 12 to 14.

The same elements as the above-mentioned embodiments are denoted by the same reference numerals and descriptions thereof will be omitted.

Figure 12A:
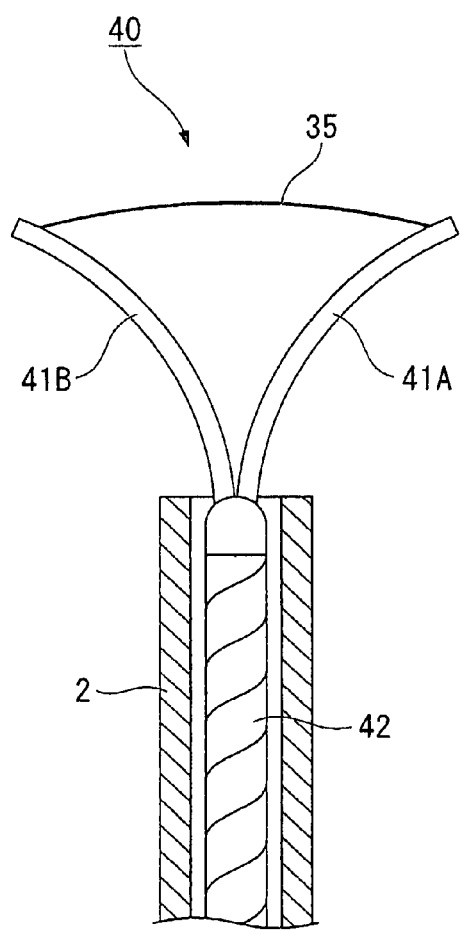
FIG. 12A is a partially-sectional plan view illustrating an opened state of a high-frequency treatment instrument according to a fourth embodiment of the invention.
Figure 12B:
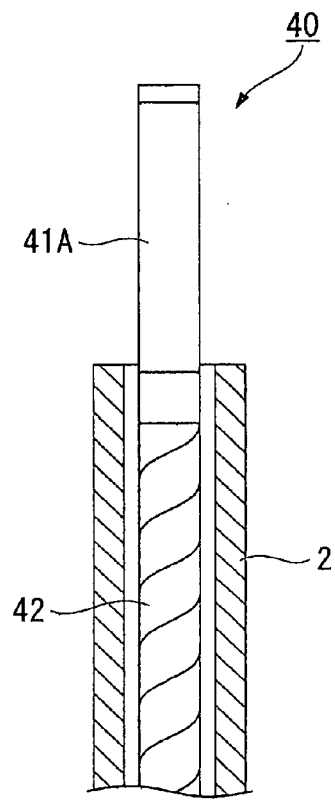
FIG. 12B is a partially-sectional side view illustrating an opened state of a high-frequency treatment instrument according to a fourth embodiment of the invention.

The fourth embodiment is different from the third embodiment, in that distal end sides of a pair of arm portions 41A and 41B of a high-frequency treatment instrument 40 according to the fourth embodiment are urged to move away from the axial core of an operating wire 42 such that the distance therebetween becomes larger than the outer diameter of the sheath 2, as shown in FIG. 12.

The pair of arm portions 41A and 41B is formed in a plate shape and the proximal ends thereof are directly fixed and connected to the distal end of the operating wire 42 by, for example, a brazing method or a laser welding method. The pair of arm portions 41A and 41B is curved outwardly in the diameter direction of the sheath 2 gradually from the proximal ends to the distal ends.

Next, operations of the high-frequency treatment instrument 40 according to this embodiment will be described.

Figure 13A:
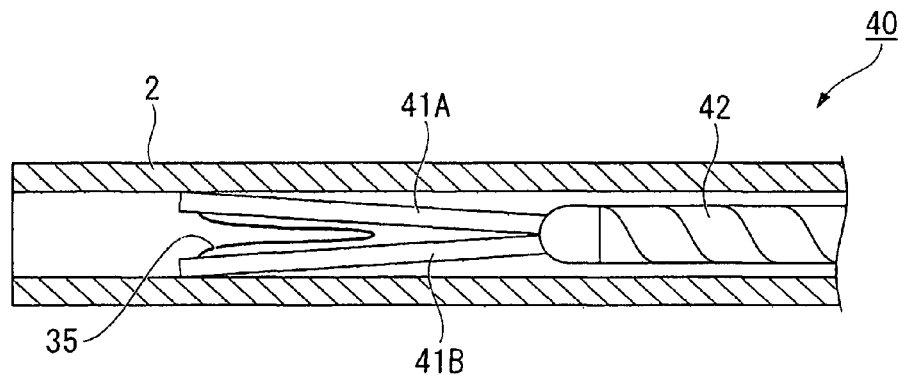
FIG. 13A is a partially-sectional plan view illustrating a closed state of the high-frequency treatment instrument according to the fourth embodiment of the invention.

First, as shown in FIG. 13A, in a state where the pair of arm portions 41A and 41B is closed and housed in the sheath 2, the treatment electrode 35 is folded and housed in the sheath 2.

Figure 13B:
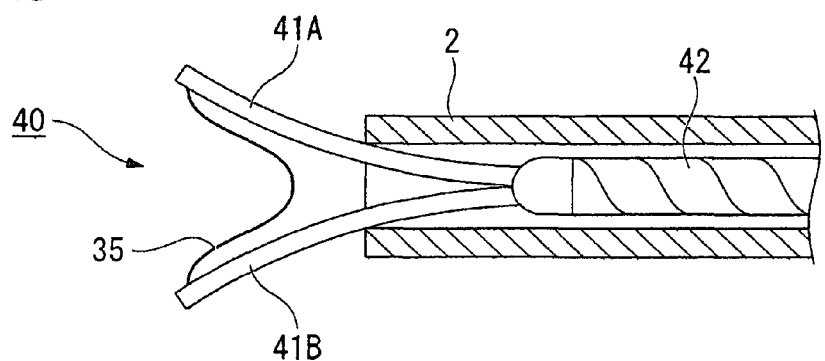
FIG. 13B is a partially-sectional plan view illustrating a state in the way of opening or closing of the high-frequency treatment instrument according to the fourth embodiment of the invention.

When the pair of arm portions 41A and 41B is opened, the operating wire 42 is made to extend toward the distal end sides relative to the sheath 2. At this time, as shown in FIG. 13B, as the distal end sides of the pair of arm portions 41A and 41B protrude from the sheath 2, the control by the sheath 2 is released and thus the distal end sides of the pair of arm portions 41A and 41B starts opening. Then, both ends of the treatment electrode 35 are drawn in the opposite directions and thus the treatment electrode 35 is gradually stretched.

Figure 13C:
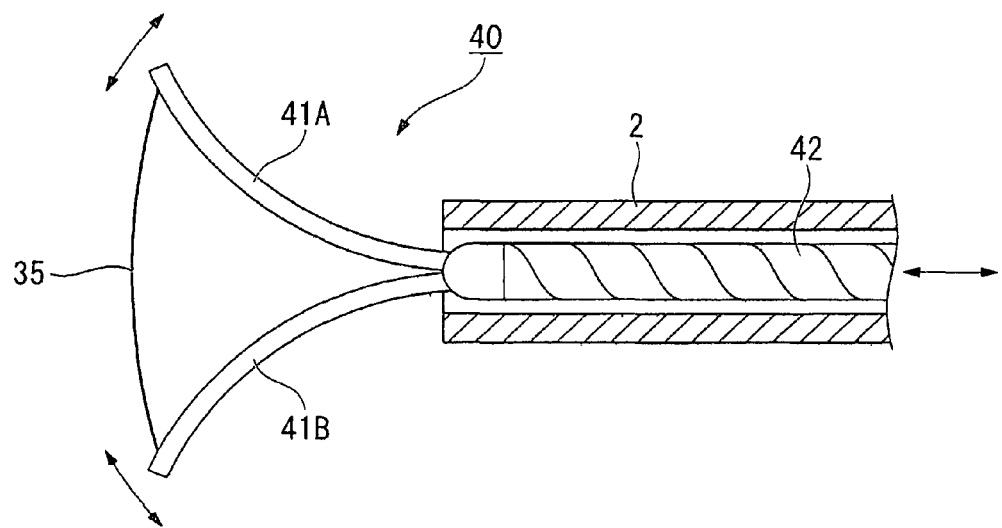
FIG. 13C is a partially-sectional plan view illustrating an opened state of the high-frequency treatment instrument according to the fourth embodiment of the invention.
Figure 14A:
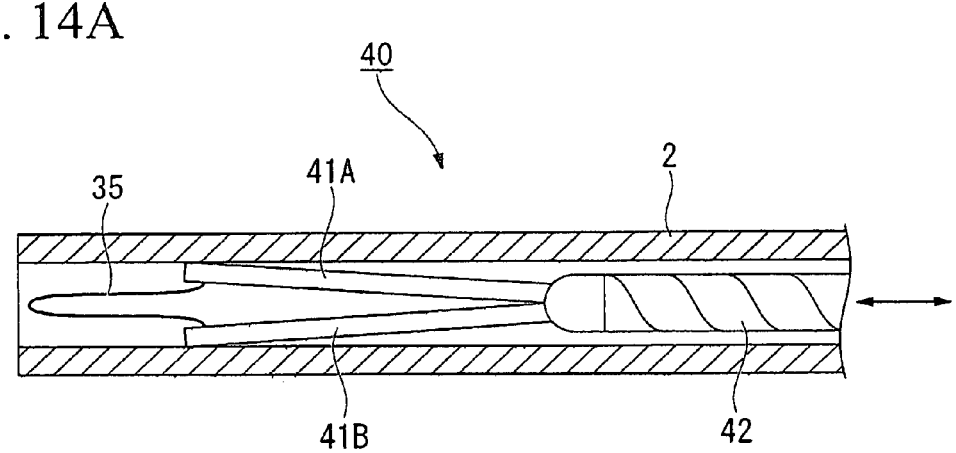
FIG. 14A is a partially-sectional plan view illustrating a closed state of the high-frequency treatment instrument according to the fourth embodiment of the invention.
Figure 14B:
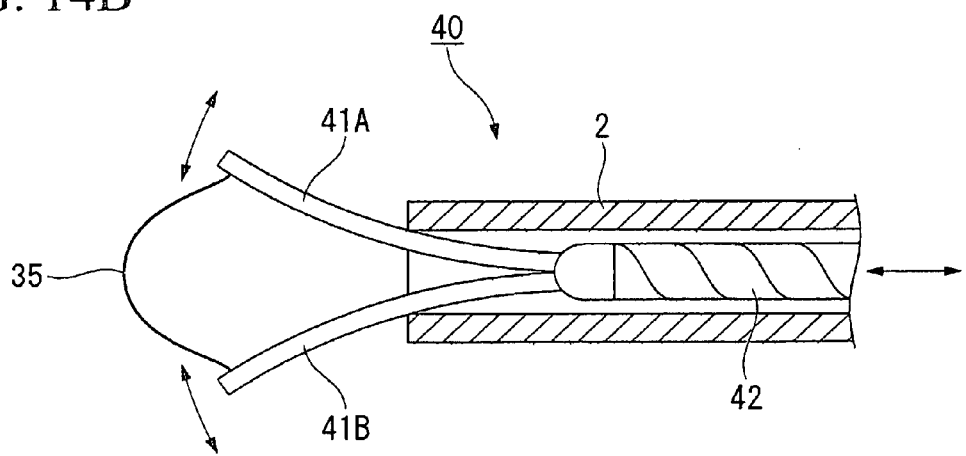
FIG. 14B is a partially-sectional plan view illustrating a state in the way of opening or closing the high-frequency treatment instrument according to the fourth embodiment of the invention.

When the entire pair of arm portions 41A and 41B protrudes from the distal end of the sheath 2, as shown in FIG. 13C, the pair of arm portions 41A and 41B are opened at a predetermined opening angle and the treatment electrode 35 is accordingly stretched between the pair of arm portions 41A and 41B. Depening on the stretched state of the treatment electrode 35, as shown in FIG. 14A, the treatment electrode 35 may be folded closer to the distal end side than the pair of arm portions 41A and 41B and may be housed in the sheath 2. In this case, as shown in FIG. 14B, the treatment electrode 35 is stretched from the distal end sides of the pair of arm portions 41A and 41B to the proximal end sides thereof.

According to the high-frequency treatment instrument 40, the treatment electrode 35 can be housed in the sheath 2 along with the pair of arm portions 41A and 41B.

Next, a fifth embodiment of the invention will be described with reference to FIG. 15.

The same elements as the above-mentioned embodiments are denoted by the same reference numerals and descriptions thereof will be omitted.

The fifth embodiment is different from the fourth embodiment, in that a short tube portion 53 through which a pair of arm portions 52A and 52B can be inserted is connected to a distal end of an operating wire 51 of a high-frequency treatment instrument 50 according to the fifth embodiment and is disposed along the outside of the sheath 55.

The short tube portion 53 has an outer diameter substantially equal to the outer diameter of the sheath 55. The length of the short tube portion 53 is adjusted so that the pair of arm portions 52A and 52B is opened at a predetermined opening angle when the short tube portion is made to move from the distal ends of the pair of arm portions 52A and 52B to a connection position to the sheath 55.

The distal ends of the pair of arm portions 52A and 52B are bent outward so as to control the separation of the short tube portion 53. The proximal ends of the pair of arm portions 52A and 52B are connected to a connection portion 55A disposed at the distal end of a sheath 55.

Next, operations of the high-frequency treatment instrument 50 according to this embodiment will be described.

Figure 15A:
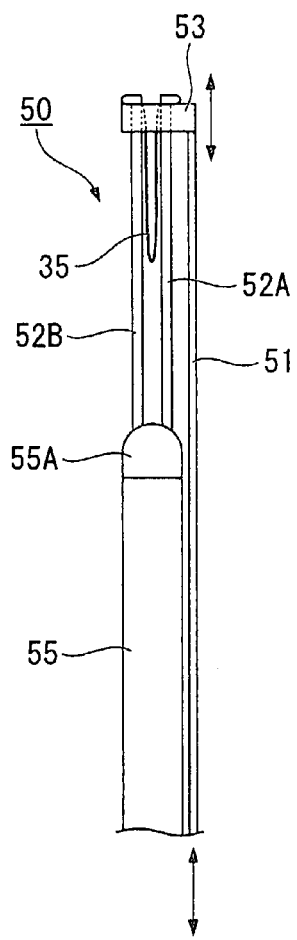
FIG. 15A is a partially-sectional plan view illustrating a closed state of a high-frequency treatment instrument according to a fifth embodiment of the invention.

First, as shown in FIG. 15A, in a state where the short tube portion 53 is moved to the distal ends of the pair of arm portions 52A and 52B, the treatment electrode 35 is folded between the pair of arm portions 52A and 52B.

Figure 15B:
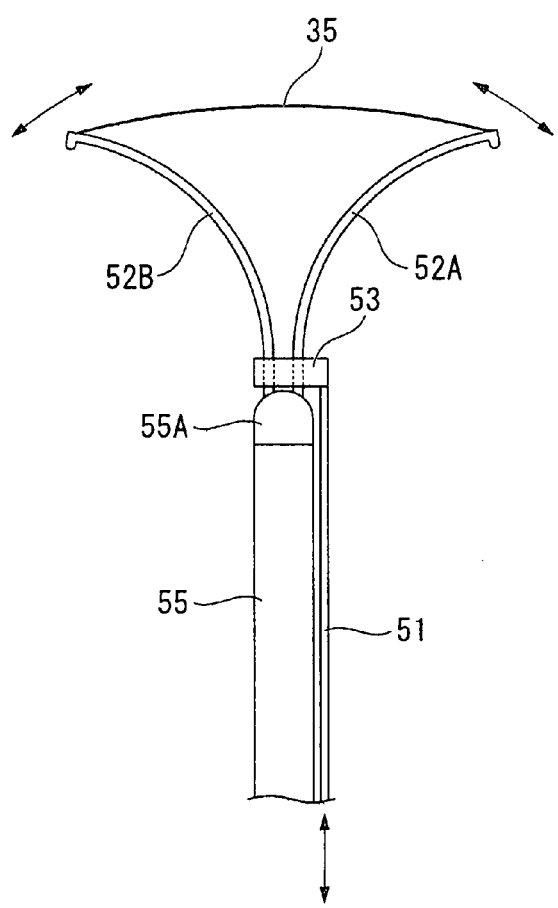
FIG. 15B is a partially-sectional plan view of substantial part illustrating an opened state of a high-frequency treatment instrument according to a fifth embodiment of the invention.

When the pair of arm portions 52A and 52B is opened, the operating wire 51 is made to retract toward the proximal end side relative to the sheath 55. At this time, the short tube portion 53 moves relative to the pair of arm portions 52A and 52B, the distal end sides of the pair of arm portions 52A and 52B protrude from the short tube portion 53 as shown in FIG. 15B, and thus the control by the short tube portion 53 is released, thereby starting opening of the distal ends of the pair of arm portion 52A and 52B. Then, both ends of the treatment electrode 35 are drawn in the opposite directions and the treatment electrode 35 is gradually stretched.

According to the high-frequency treatment instrument 50, similarly to the fourth embodiment, the same advantages can be obtained by operating the operating wire 51 to extend and retract relative to the sheath 55.

Next, a sixth embodiment of the invention will be described with reference to FIGS. 16 to 19.

The same elements as the above-mentioned embodiments are denoted by the same reference numerals and descriptions thereof will be omitted.

Figure 16A:
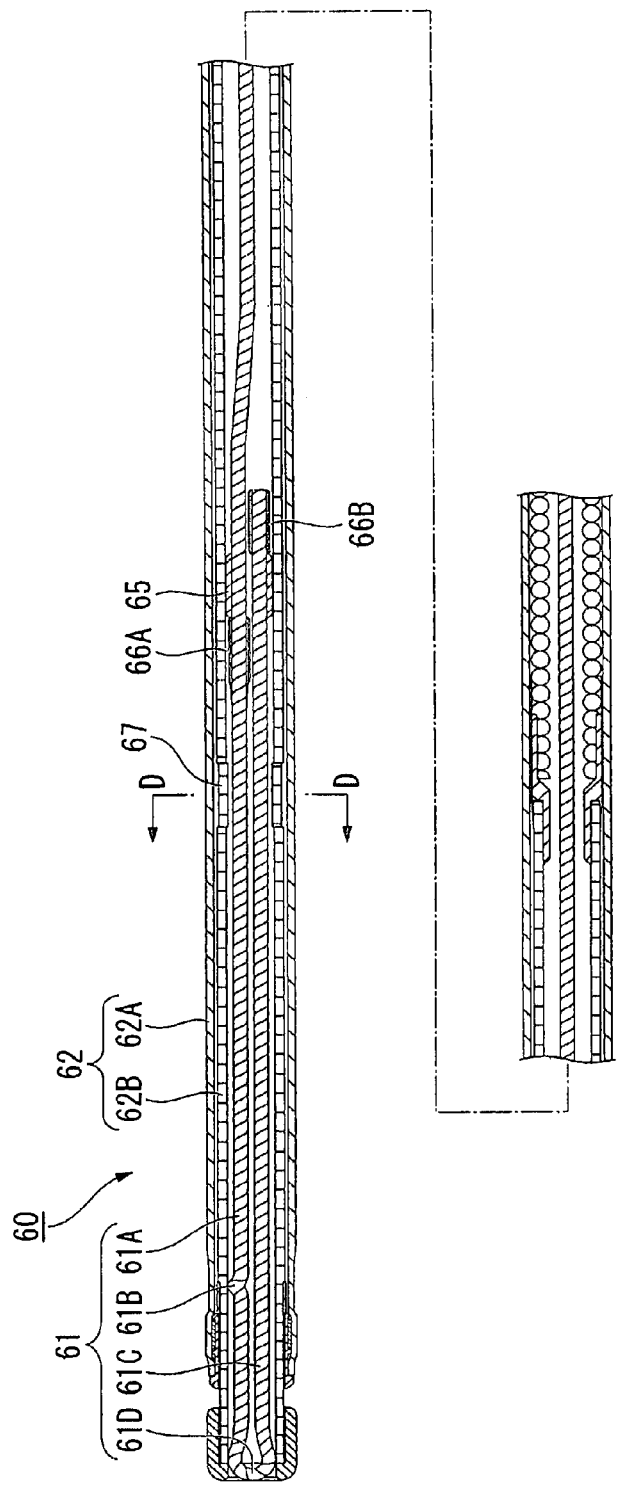
FIG. 16A is a sectional view illustrating a high-frequency treatment instrument according to a sixth embodiment of the invention.
Figure 16B:
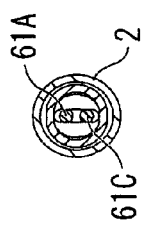
FIG. 16B is a cross-sectional view taken along line D-D of FIG. 16A.

The sixth embodiment is different from the first embodiment, in that a high-frequency treatment instrument 60 according to this embodiment does not include the pair of arm portions 3A and 3B as in the first embodiment but an operating wire 61 includes a first linear portion 61A disposed along a sheath 62, a first bent portion 61B formed at the distal end of the first linear portion 61A, a second linear portion 61C extending from the first bent portion 61B, and a second bent portion 61D formed halfway along the second linear portion 61C, as shown in FIG. 16.

The operating wire 61 is usually housed in the sheath 62 in a state where it is folded back at the second bent portion 6 ID and the distal end of the second linear portion 61C is disposed to extend halfway along the first linear portion 61A. When the first linear portion 61A and the second linear portion 61C are made to extend toward the distal end direction of the sheath 62 and the first bent portion 61B and the second bent portion 61D are made to protrude from the sheath 62, a treatment electrode 63 substantially perpendicularly intersecting with a center axial line C of the sheath 62 is formed between the first bent portion 61B and the second bent portion 61D.

Pressing members 66A and 66B between which a tube-shaped diameter-enlarged portion (control portion) 65 controlling a protruding amount of the first linear portion 61A and the second linear portion 61C from the distal end of the sheath 62 are disposed halfway along the first linear portion 61A and at the distal end of the second linear portion 61C. The outer diameters of the pressing members 66A and 66B are larger than the inner diameter of the diameter-enlarged portion 65.

The sheath 62 includes an outer sheath 62A and an inner sheath 62B which the inner side of the outer sheath 62A covers. A narrow tube portion 67 which allows the pressing members 66A and 66B to pass therethrough but controlling the movement of the diameter-enlarged portion 65 toward the distal end side of the sheath 62 is disposed halfway along the inner sheath 62B. A cover 68, distal end of which having a curved surface, is disposed at the distal end of the inner sheath 62B. A cap 69 is disposed at the distal end of the outer sheath 62A.

Figure 19:
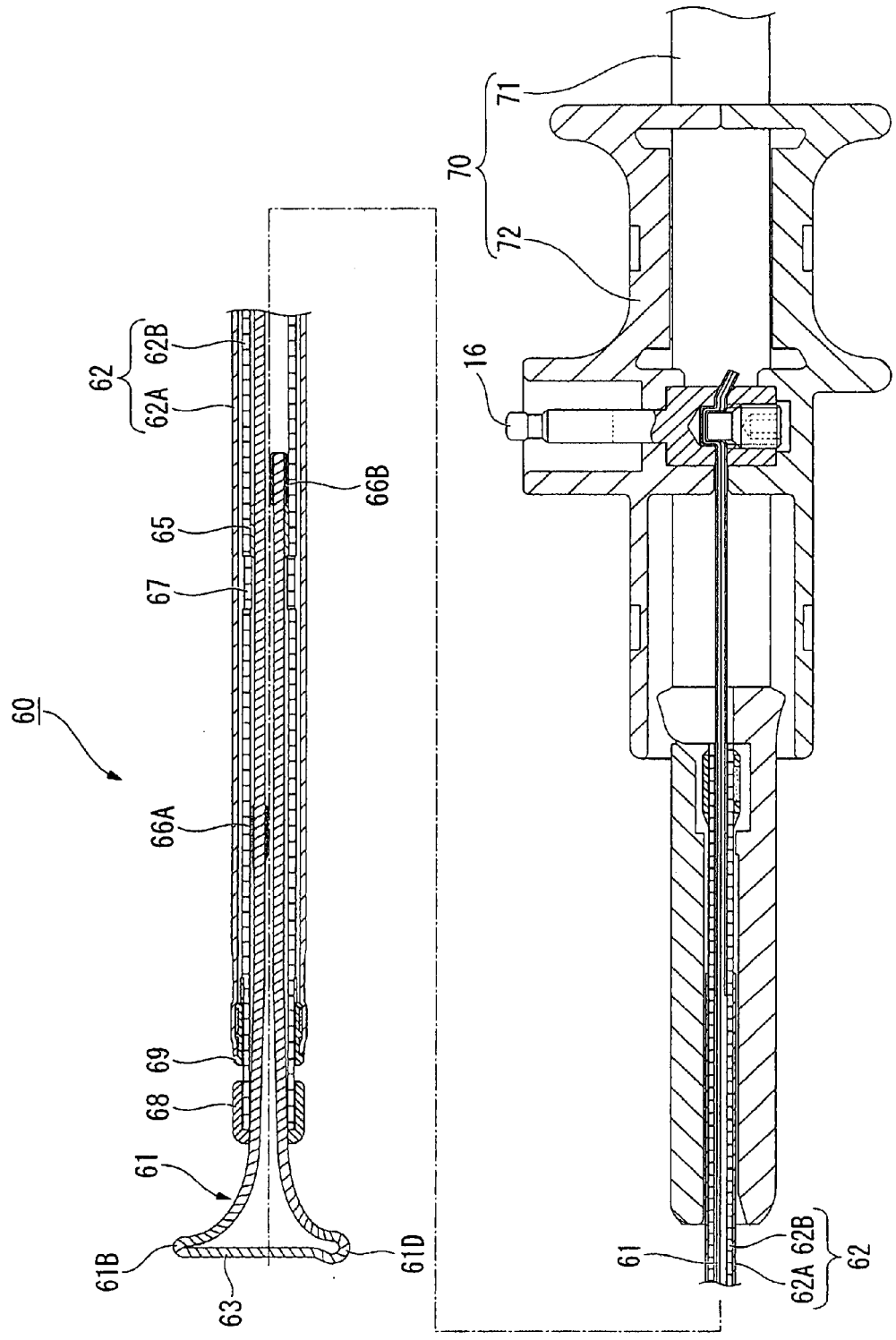
FIG. 19 is a sectional view illustrating an opened state of the high-frequency treatment instrument according to the sixth embodiment of the invention.

An operating portion 70 includes a rod-shaped operating portion body 71 a distal end of which is connected to the proximal end of the sheath 62 and a slider 72 connected to the proximal end of the operating wire 61, as shown in FIG. 19. The slider 72 is covered onto the operating portion body 71 so as to freely slide and is connected such that the inner sheath 62B and the operating wire 61 are rotatable relative to the outer sheath 62A.

An electrode terminal 16 is disposed in the slider 72.

Next, operations of the high-frequency treatment instrument 60 according to this embodiment will be described.

Figure 17:
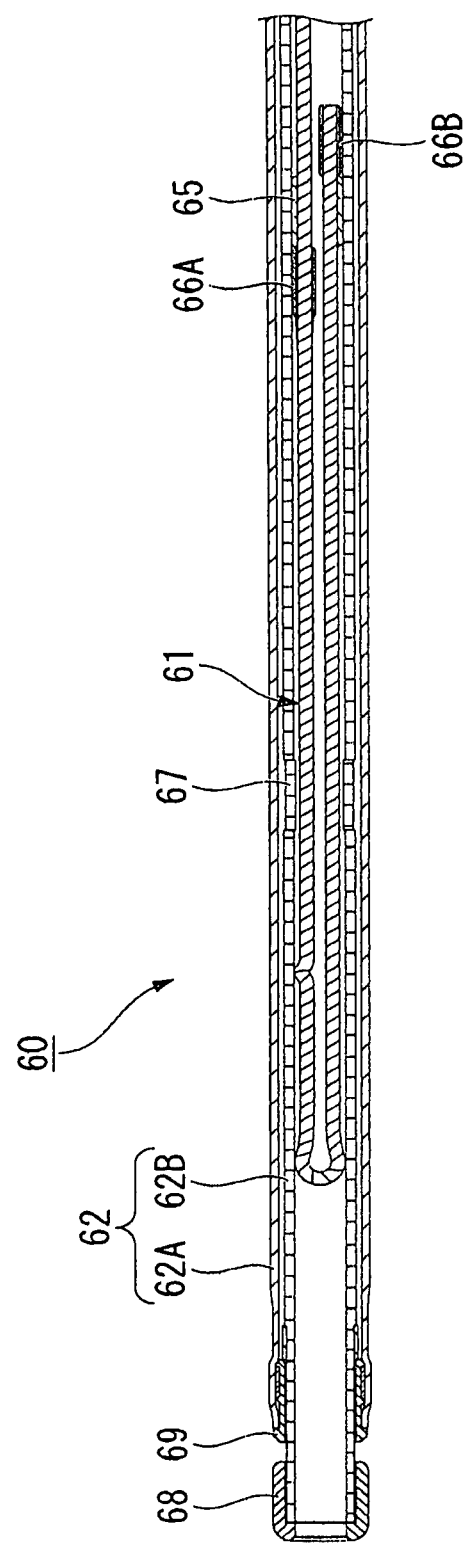
FIG. 17 is a sectional view illustrating a closed state of the high-frequency treatment instrument according to the sixth embodiment of the invention.

When the treatment electrode 63 is to be formed, as shown in FIG. 17, the distal end side of the high-frequency treatment instrument 60 is made to protrude from a treatment instrument channel not shown in a state where the entire operating wire 61 is housed in the sheath 62, the slider 72 is pushed out relative to the operating portion body 71, and thus the operating wire 61 is made to extend relative to the sheath 62. At this time, as shown in FIG. 16A, the first linear portion 61A and the second linear portion 61C move together toward the distal end of the sheath 62.

Figure 18:
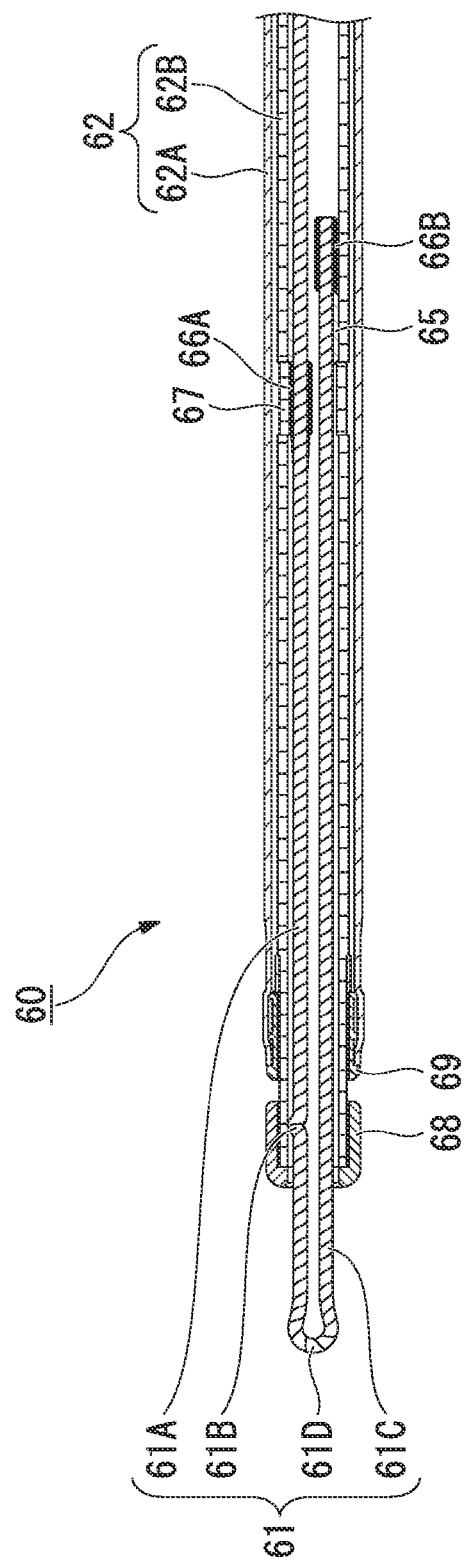
FIG. 18 is a sectional view illustrating a state in the way of opening or closing of the high-frequency treatment instrument according to the sixth embodiment of the invention.

As shown in FIG. 18, when the second bent portion 61D protrudes from the distal end of the sheath 62 by a predetermined length, the diameter-enlarged portion 65 comes in contact with the narrow tube portion 67. Accordingly, the second linear portion 61C is fixed to the sheath 62. On the other hand, the pressing member 66A passes through the narrow tube portion 67. Accordingly, the first bent portion 61B is more bent just after the moment that the first bent portion 61B has protruded from the sheath 62, and the second linear portion 61C between the first bent portion 61B and the second bent portion 61D rotates as the second bent portion 61D being the center of rotation to a direction which is substantially perpendicular to the center axial line C of the sheath 62.

In this way, as shown in FIG. 19, the treatment electrode 63 is formed between the first bent portion 61B and the second bent portion 61D. When a cut-out angle is to be changed, the operating portion 70 is made to rotate relative to the outer sheath 62A, thereby changing the direction of the treatment electrode 63 relative to a pathological lesion portion not shown.

According to the high-frequency treatment instrument 60, the same advantages as the first embodiment can be obtained.

As shown in FIG. 18, in the state where the diameter-enlarged portion 65 and the narrow tube portion 67 come in contact with each other, the first linear portion 61A and the second linear portion 61C remain to be substantially parallel to the sheath 62 and extend from the sheath 62, with the second bent portion 61D as a distal end thereof. Accordingly, by supplying high-frequency current to the treatment electrode 63, it is possible to obtain the same operations and advantages as the existing high-frequency knife.

The technical scope of the invention is not limited to the above-mentioned embodiments, but various modifications may be made therein without departing from the gist of the invention.

For example, in the first embodiment, not only the one of the pair of arm portions 3A but also the other of the pair of arm portions 3B is formed in a tube shape, but the other of the pair of arm portions 3B may not be formed in a tube shape as long as one end of the treatment electrode is fixed to the other of the pair of arm portions 3B.

Figure 20:
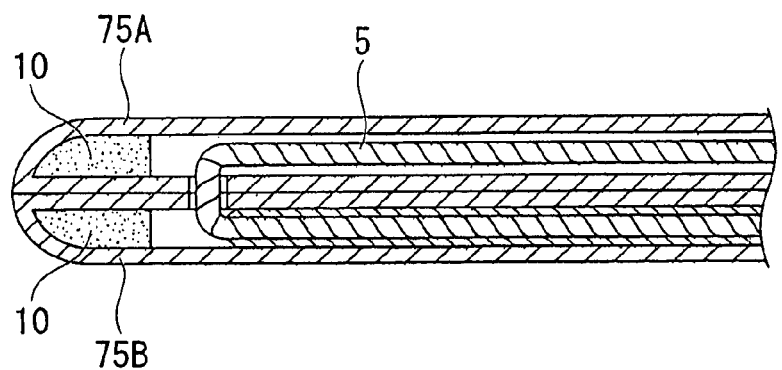
FIG. 20 is an enlarged sectional view illustrating a modified example of the high-frequency treatment instrument according to the first embodiment of the invention.
Figure 21:
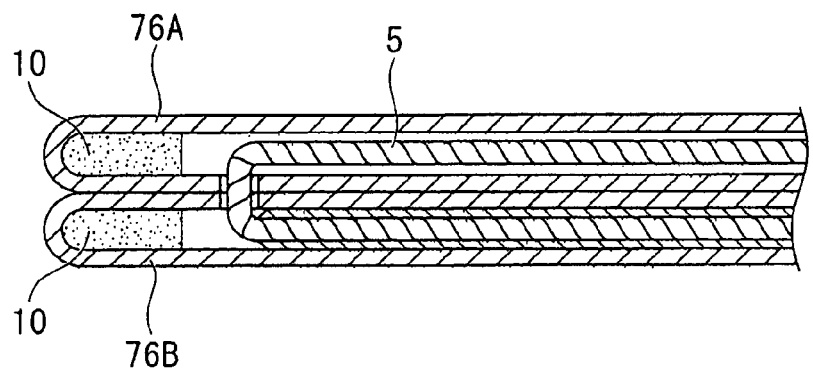
FIG. 21 is an enlarged sectional view illustrating a modified example of the high-frequency treatment instrument according to the first embodiment of the invention.

Although the shape of the distal ends of the pair of arm portions have a chamfered shape in which the distal ends are cut out as shown in FIG. 1, distal ends of a pair of arm portions 75A and 75B may be chamfered to form a single circular curvature in a closed state as shown in FIG. 20. Alternatively, each distal end of a pair of arm portions 76A and 76B may be chamfered to form a circular curvature as shown in FIG. 21.

According to the first aspect of the invention, when the pair of arm portions is made to protrude from the distal end of the sheath and is thus opened, the treatment electrode can be stretched in a direction intersecting with the center axial line of the sheath at the distal end sides of the pair of arm portions. Accordingly, when the pair of arms are operated to extend and retract relative to the sheath with the treatment electrode stretched, it is possible to increase a contact area between the treatment electrode and the target tissue compared to the conventional techniques.

According to the second aspect of the invention, it is possible to interpose the target tissue in the bent portion and thus it is possible to bring the treatment electrode into stable contact with the target tissue.

According to the third aspect of the invention, by allowing the treatment electrode to extend and retract relative to the one of the pair of arm portions, it is possible to open and close the pair of arm portions by means of an axial tension generated in the treatment electrode. At this time, it is possible to house the treatment electrode in at least one of the pair of arm portions with the pair of arm portions closed.

According to the fourth aspect of the invention, by operating the elongated extension member so as to extend and retract relative to the sheath, it is possible to allow the treatment electrode to extend and retract relative to the one of the pair of arm portions.

According to the fifth aspect of the invention, when the pair of arm portions is opened, the treatment electrode can be stretched in a direction intersecting with an axial core of the elongated extension member at the distal end sides of the pair of arm portions. Accordingly, when the pair of arm portions is operated to extend and retract with the treatment electrode stretched, it is possible to increase the contact area between the treatment electrode and the target tissue compared to the conventional techniques.

According to the sixth aspect of the invention, it is possible to open and close the pair of arm portions by allowing the pair of arm portions to extend and retract relative to the sheath.

According to the seventh aspect of the invention, when the first linear portion of the elongated extension member is made to move in a direction protruding from the distal end of the sheath, it is possible to open the proximal end side of the second linear portion relative to the first linear portion using the first bent portion as an opening and closing center and to allow the second linear portion to intersect with the center axial line of the sheath.

According to the eighth aspect of the invention, since the treatment electrode is disposed in a position intersecting with the center axial line of the sheath, it is possible to increase the contact area between the treatment electrode and the target tissue compared to the conventional techniques.

According to the ninth aspect of the invention, it is possible to adjust the protruding amount of the first linear portion and the second linear portion from the sheath by the use of the control portion.

According to the invention, it is possible to facilitate a procedure by enabling a treatment on a target tissue without performing a curving operation of an endoscope.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A high-frequency treatment instrument comprising:
   a sheath;
   an elongated extension member which is disposed in the sheath so as to freely extend and retract, the elongated extension member including:
      a first linear portion disposed along the sheath, the first linear portion having a proximal end at a proximal side of the sheath and a distal end at a distal side of the sheath,
      a first bent portion formed at the distal end of the first linear portion,
      a third linear portion extending from the first bent portion toward a distal end of the sheath, the third linear portion having a proximal end at the proximal side of the sheath and a distal end at the distal end of the sheath,
      a second bent portion formed at the distal end of the third linear portion, and
      a second linear portion extending from the second bent portion, the second linear portion having a distal end at the proximal side of the sheath and a proximal end at the distal side of the sheath, and
   a narrow portion provided on an inner surface of the sheath, wherein
      a pressing member is provided on the second linear portion, wherein the pressing member allows the distal end of the second linear portion to advance and retract only in a part of the sheath, wherein the part of the sheath is located proximal to the narrow portion,
      when the second bent portion is protruded from the sheath while the first bent portion is inside of the sheath, a portion of the elongated extension member which protrudes from the sheath becomes a first treatment electrode which extends along a center axial line of the sheath, and
      when the elongated extension member is advanced after the first treatment electrode is formed, the first bent portion protrudes from the sheath while advancement of the pressing member and the second linear member is suppressed by the narrow portion, and a part of the first treatment electrode between the first bent portion and the second bent portion becomes a second treatment electrode which intersects with the center axial line of the sheath,
   wherein the high-frequency treatment instrument further comprises:
      a control portion, which controls a protruding amount of the third linear portion and the second linear portion from the distal end of the sheath by directly contacting the narrow portion, is disposed at a position that is closer to a proximal end of the sheath than the second bent portion,
         wherein the control portion is configured to be moved by movement of the first linear portion and the second linear portion toward a distal opening of the sheath until the control portion is moved into direct contact with the narrow portion.

2. A treatment instrument comprising:
   a sheath having a distal end and a proximal end,
      wherein the sheath is comprised of a sheath inner wall defining a sheath inner space extending along a longitudinal axis between the distal end and the proximal end,
      wherein the sheath inner space opens to a sheath distal opening at the distal end of the sheath, and
      wherein the sheath inner wall comprises an intermediate portion, a distal portion arranged distally of the intermediate portion along the longitudinal axis, and a proximal portion arranged proximally of the intermediate portion along the longitudinal axis;
   a control tube configured to be guided by the proximal portion of the sheath inner wall to move along the longitudinal axis and to abut against the intermediate portion of the sheath inner wall; and
   an operation wire comprising, in order between a first end of the operation wire and a second end of the operation wire: a first linear portion, a first bent portion, a second linear portion, a second bent portion, and a third linear portion; and
   a pressing member fixed to the third linear portion of the operation wire,
      wherein the pressing member is configured to be arranged in the sheath inner space at a position proximal to the control tube along the longitudinal axis and to abut against the control tube,
   wherein the sheath, the control tube, the operation wire and the pressing member are configured to be arranged in a first configuration, a second configuration and a third configuration,
   wherein in the first configuration, the second bent portion of the operation wire is arranged within the sheath inner space at a more distal position along the longitudinal axis than the second linear portion and the third linear portion,
   wherein in the second configuration:
      the control tube is guided by the proximal portion of the sheath inner wall to abut against the intermediate portion of the sheath inner wall to limit movement of the control tube in a distal direction along the longitudinal axis, and
      the pressing member abuts against the control tube to limit movement of the third linear portion of the operation wire in the distal direction along the longitudinal axis such that the second bent portion of the operation wire is exposed through the sheath distal opening sheath and the first bent portion of the operation wire is maintained within the sheath inner space, and wherein in the third configuration:
- the control tube remains abutted against the intermediate portion of the sheath inner wall to limit movement of the control tube in the distal direction along the longitudinal axis,
- the pressing member remains abutted against the control tube to limit movement of the third linear portion of the operation wire in the distal direction along the longitudinal axis such that the second bent portion of the operation wire remains exposed through the sheath distal opening and
- the first linear portion of the operation wire is moved in the distal direction along the longitudinal axis such that the first bent portion and the second linear portion are exposed through the sheath distal opening.

\* \* \* \* \*